(12) United States Patent
Guertin et al.

(10) Patent No.: US 8,330,132 B2
(45) Date of Patent: Dec. 11, 2012

(54) ENERGY MODULATOR FOR MODULATING AN ENERGY OF A PARTICLE BEAM

(75) Inventors: Timothy Guertin, Saratoga, CA (US); Marcel Marc, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 785 days.

(21) Appl. No.: 12/199,698

(22) Filed: Aug. 27, 2008

(65) Prior Publication Data

US 2010/0051833 A1    Mar. 4, 2010

(51) Int. Cl.
*G21F 3/00*    (2006.01)

(52) U.S. Cl. .................. 250/515.1; 250/505.1; 378/156; 378/203

(58) Field of Classification Search ............... 250/505.1, 250/506.1, 515.1, 517.1, 518.1, 519.1; 378/156, 378/203

See application file for complete search history.

(56) References Cited

U.S. PATENT DOCUMENTS

| | | | |
|---|---|---|---|
| 2002/0125429 A1* | 9/2002 | Lebrun et al. | 250/336.1 |
| 2004/0200983 A1* | 10/2004 | Fujimaki et al. | 250/492.3 |
| 2004/0200997 A1* | 10/2004 | Soundararajan | 252/478 |
| 2006/0284122 A1* | 12/2006 | Caldwell | 250/515.1 |
| 2008/0048135 A1* | 2/2008 | Cernasov | 250/515.1 |
| 2009/0289192 A1* | 11/2009 | Westerly et al. | 250/396 R |
| 2009/0299634 A1* | 12/2009 | Schaffner | 702/1 |

\* cited by examiner

*Primary Examiner* — Robert Kim
*Assistant Examiner* — Nicole Ippolito
(74) *Attorney, Agent, or Firm* — Vista IP Law Group, LLP

(57) ABSTRACT

An energy modulator for use with a particle source that provides a beam of particles includes a first block moveable between a first position and a second position, wherein when the first block is at the second position, it is in a path of the beam, and a second block moveable relative to the first block, wherein the second block and the first block are offset from each other in a direction of the beam, wherein the first block has a first energy absorption characteristic, and the second block has a second energy absorption characteristic that is different from the first energy absorption characteristic.

52 Claims, 9 Drawing Sheets

ENERGY MODULATOR FOR MODULATING AN ENERGY OF A PARTICLE BEAM

FIELD

The field relates generally to systems and methods for modulating an energy of a particle beam, such as a proton beam.

BACKGROUND

Radiation therapy has been employed to treat tumorous tissue. In radiation therapy, a high energy beam is applied from an external source towards the patient. The external source produces a collimated beam of radiation that is directed into the patient to the target site. The dose and placement of the dose must be accurately controlled to ensure that the tumor receives sufficient radiation, and that damage to the surrounding healthy tissue is minimized.

Existing radiotherapy systems use x-ray as the radiation beam. In such systems, the ability to control the dose placement is limited by the physics of the beam, which necessarily irradiates healthy tissue on the near-side and far-side of a target region as it passes through the patient. Thus, it may be desirable to use protons as the source of the radiation. By controlling the energy of the protons, the protons will stop at a precise location within the patient. In this way, tissue on the far-side of the target region does not receive any radiation dose. Further, because the dose provided by a proton is concentrated at a "Bragg peak" around the area where the proton stops, the dose to healthy tissue on the near-side of the target region may also be reduced.

Sometimes, it may be desirable to selectively modulate an energy of the proton beam such that the Bragg peak can hit target regions that are located at different depths in the patient. Also, if proton technique is to be used to implement arc therapy, in which the beam source is rotated about the target region, it may also be desirable to selectively modulate the energy of the proton beam dynamically during the treatment procedure. This is especially the case if the target region is closer to one side of the patient than others. In this case, the proton beam may need to penetrate less tissue to reach the target region at certain gantry angle, and more tissue at other gantry angles. However, existing proton systems do not allow an energy of the beam to be modulated accurately, reliably, and effectively during a treatment procedure.

SUMMARY

In accordance with some embodiments, an energy modulator for use with a particle source that provides a beam of particles includes a first block moveable between a first position and a second position, wherein when the first block is at the second position, it is in a path of the beam, and a second block moveable relative to the first block, wherein the second block and the first block are offset from each other in a direction of the beam, wherein the first block has a first energy absorption characteristic, and the second block has a second energy absorption characteristic that is different from the first energy absorption characteristic.

In accordance with other embodiments, an energy modulator for use with a particle source that provides a beam of particles includes a first block moveable between a first position and a second position, wherein when the first block is at the second position, it is in a path of the beam, and a second block moveable relative to the first block, wherein the second block and the first block are offset from each other in a direction of the beam, wherein the first block and the second block are at least partially transparent to the particle beam, the first block having a surface that is perpendicular to the beam.

In accordance with other embodiments, an energy modulator for use with a particle source that provides a beam of particles includes a first block moveable between a first position and a second position, wherein when the first block is at the second position, it is in a path of the beam, and a second block moveable relative to the first block, wherein the second block and the first block are offset from each other in a direction of the beam, wherein the first block and the second block are at least partially transparent to the particle beam, and wherein the first block is made from a first material, the second block is made from a second material that is different from the first material.

In accordance with other embodiments, a method for modulating an energy of a particle beam includes determining information regarding a desired particle beam energy, determining a combination of blocks to be placed in a path of a beam based on the determined information, wherein the blocks are offset from each other in a direction of the beam, and positioning the blocks such that they are in the path of the beam.

In accordance with other embodiments, a method for modulating an energy of a particle beam includes providing a first modulator that is located closer to a particle source than a nozzle, providing a second modulator that is located closer to the nozzle than the particle source, operating the first modulator when an energy of the beam is desired to be decreased, and operating the second modulator when the energy of the beam is desired to be increased.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
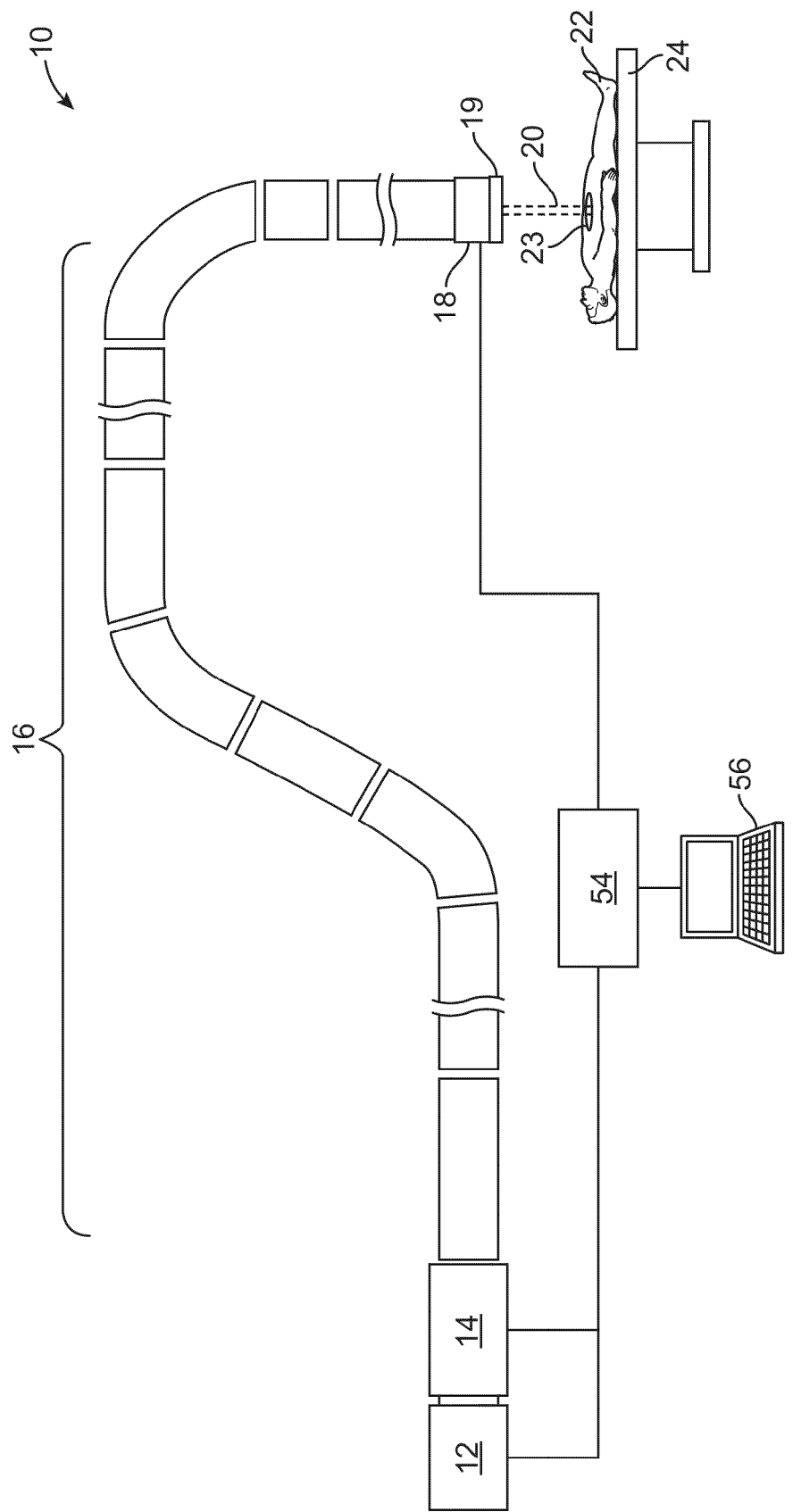
FIG. 1 is a block diagram of a proton system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Referring now to the drawings, in which similar or corresponding parts are identified with the same reference numeral, FIG. 1 illustrates a proton system 10, in accordance with some embodiments. The proton system 10 includes a proton generator 12, an energy modulator 14, a beam transport system 16, and a nozzle 18. The proton generator 12 is for providing accelerated protons, which may be transported to a target by the beam transport system 16. The beam transport system 16 also includes a plurality of magnets for steering the proton beam to a desired location, e.g., a particular treatment room. The accelerator may be a cyclotron, which provides a fixed energy, or alternatively, a synchrotron, which provides variable energy. Typically, the beam transport system 16 may be used for guiding the beam to more than one treatment rooms. The nozzle 18 is mounted on a gantry (e.g., a rotatable gantry) or a fixed beam port. The nozzle 18 is for adjusting the proton beam so that the beam 20 has a certain desired characteristic for treating a target region 23 within the patient 22 who is supported on a patient support 24. The nozzle 18 includes a collimator 19, which is for blocking at least some of the beam so that the resulting beam conforms to a shape of a target region. In the illustrated embodiments, the collimator 19 comprises a multi-leaf collimator, and includes a plurality of leafs or fingers that are slidable relative to each other. During use, the leafs are positioned to thereby form a desired shape of an opening for allowing the beam to pass through the collimator 19. In other embodiments, the collimator 19 may be a single block having an opening that is predetermined. The collimator 19 may be made from brass or other materials.

The energy modulator 14 is shown as a separate component as the proton generator 12 and the beam transport system 16, but may be integrated with the proton generator 12 (in which case, the energy modulator 14 will be a part of the proton generator 12) or with the beam transport system 16 (in which case, the energy modulator 14 will be a part of the beam transport system 16).

The system 10 also includes a processor 54, which may be used to control an operation of the proton source 12, the energy modulator 14, and/or an operation of the nozzle 18. In some cases, the processor 54 may also be used to obtain data regarding an operation of the proton machine, perform analysis and calculation on dose, and other functions, such as those described herein. The system 10 may also include an user interface 56 having a monitor and an input device (e.g., keyboard, mouse, etc.) for allowing a user to input and receive data.

Figure 2:
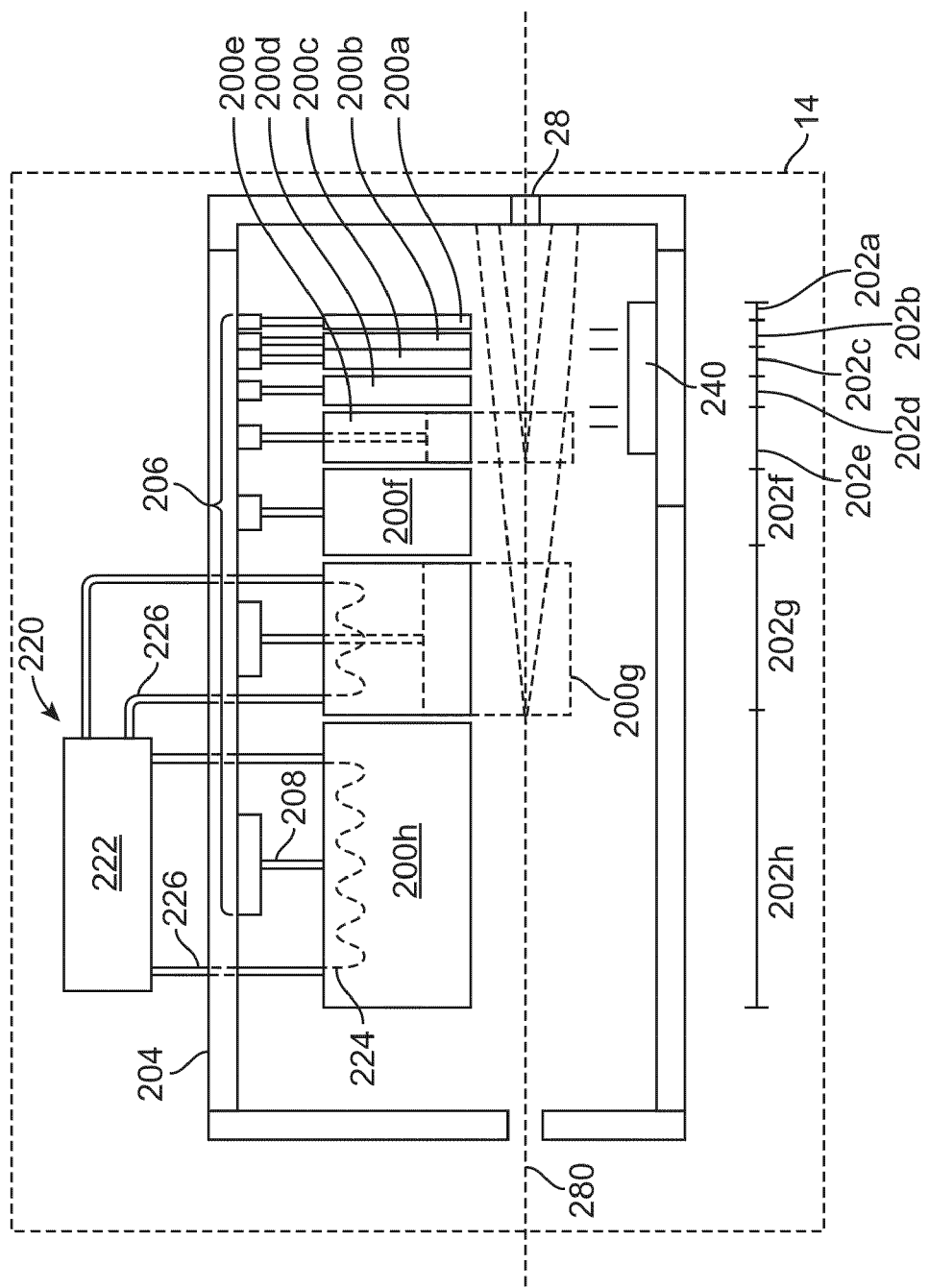
FIG. 2 illustrates an energy modulator in accordance with some embodiments.

FIG. 2 illustrates the energy modulator 14 in accordance with some embodiments. The energy modulator 14 includes a plurality of blocks 200. In the illustrated embodiments, the energy modulator 14 includes eight blocks 200a-200h. In other embodiments, the energy modulator 14 may have other number of blocks, e.g., as many as 100 blocks or more. The blocks 200a-200h have respective thicknesses 202a-202h, wherein thickness 202h is two times the thickness 202g, thickness 202g is two times the thickness 202f, thickness 202f is two times the thickness 202e, thickness 202e is two times the thickness 202d, thickness 202d is two times the thickness 202c, thickness 202c is two times the thickness 202b, and thickness 202b is two times the thickness 202a. Thus, the blocks 200 have respective thicknesses 202h that collectively form a logarithmic pattern. Each of the blocks 200 may be individually moved between a first position and a second position, wherein when the block 200 is in the first position, the block 200 is not in a path of a beam 280, and when the block 200 is in the second position, it is in the path of the beam 280. Such binary configuration provides $2^N$ variations of energy modulation, wherein N equals to the total number of blocks 200. In the example shown in the figure, there are eight blocks 200 (i.e., with N=8), providing $2^8$=256 variations of energy modulation for the beam 280. In the illustrated embodiments, the blocks 200 are offset from each other in a direction of the beam 280. This configuration allows different blocks 200 to enter into the beam path at different locations along the beam line. As used in this specification, the term "offset" refers to any spacing between a reference point on one block 200 and a reference point on another block 200.

The energy modulator 14 also includes a mounting structure 204 to which the blocks 200 are moveably mounted, and a positioning system 206 for moving the blocks 200. The positioning system 206 includes a plurality of arms 208 that are coupled to respective blocks 200. The positioning system 206 may include a plurality of pistons for moving the arms 208. The pistons may be driven by hydraulics, electric motors, piezoelectric motors, or other devices known in the art. If a motor is used, the motor may be a linear-type motor or a rotating-type motor. In other embodiments, the pistons may be driven pneumatically (e.g., by a pneumatic mechanism). In the illustrated embodiments, the arms 208 are located on a same side of the energy modulator 14. In other embodiments, the arms 208 may be located on different sides of the energy modulator 14. Such configuration provides more space to accommodate the arms 208 and other associated components for the blocks 200.

The blocks 200 have different respective energy absorption characteristics. Each of the blocks 200 is made from a material that allows at least part of the proton beam to be transmitted therethrough while slowing down the protons. By means of non-limiting examples, the blocks 200 may be made from plastic(s), metal(s), graphite(s), other composite materials, or other suitable materials. In some cases, the relatively larger block(s) may be made from any conductive material(s). In some embodiments, all of the blocks 200 are made from the same material. In other embodiments, one or more of the blocks 200 may be made from a material that is different from the material of other block(s) 200. For example, in some embodiments, the thicker block(s) may be made from a first material with a Z value that is less than a Z value of a second material for the thinner block(s) 200. In such cases, the thicknesses and the materials of the blocks 200 are selected such that the change of energies affected by the respective blocks 200 form a logarithmic pattern. For example, in other embodiments, block 200h may have the same thickness as that of block 200g. However, the materials for blocks 200h and 200g may be different (e.g., the material for block 200h may have a lower Z value than that of the material for block 200g), such that the change of energy ($\Delta E_h$) affected by block 200h is twice as that of the change of energy ($\Delta E_g$) affected by block 200g. Similarly, the material and the thickness of block 200f may be selected such that the energy ($\Delta E_g$) affected by block 200g is twice as that of the change of energy ($\Delta E_f$) affected by block 200f, and so forth for the remaining blocks 200. Thus, the energy absorption characteristic for each of the blocks 200 may be accomplished by thickness selection, material selection, or both.

In some embodiments, the material(s) and thickness(es) for the blocks 200 are selected such that the set of blocks 200 provide for the beam a total range of energy modulation $\Delta E_{Total}$ that is between 40 kV and 600 MeV for protons, and between 40 kV and 1 GeV power nucleons for other ions (e.g., Carbon). Thus, if the beam has an initial energy $E_{initial}$, the use of the energy modulator 14 (i.e., to place the block(s) 200 in, or to remove the block(s) from, the beam path) may create a beam with energy $E_{modulated} = E_{initial} \pm \Delta E_{Total}$. For example, placing only the thinnest block 200a into the path of the beam would allow the energy of the beam to be decreased by as little as 5 kV, while placing all of the blocks 200 into the beam path would allow the energy of the beam to be decreased by as much as 200 MeV. Similarly, in another example, removing only the thinnest block 200a from the path of the beam would allow the energy of the beam to be increased by as little as 5 kV, while removing all of the blocks 200 from the beam path would allow the energy of the beam to be increased by as much as 200 MeV. In some cases, the thinnest block 200a may have a thickness that is less than 10 cm, e.g., less than 1 cm. In some embodiments, the use of the energy modulator 14 provides a beam at the nozzle 18 having an energy that is between 70 MeV and 250 MeV, which corresponds to tissue penetration that is between 4 cm and 38 cm.

In the above embodiments, the blocks 200 are arranged such that the block 200h with the largest thickness 202h is closest to the particle source 12, with the remaining blocks 200a-200g being arranged further away from the particle source 12 in accordance with their decreasing thicknesses. In other embodiments, the blocks 200 may be arranged differently. For example, in other embodiments, the blocks 200 may be arranged in increasing thicknesses as they are placed further away from the particle source 12. Also, in other embodiments, the blocks 200 may not be arranged in increasing or decreasing thicknesses. Further, in other embodiments, the blocks 200 need not abut against one another as that shown in the figure, and may be spaced away from each other. In such cases, the gap (e.g., 0.5 mm to 20 cm) between the blocks 200 may allow at least some of the blocks 200 to be cooled by convection more efficiently. Spacing the blocks 200 away from each other also has the benefit of allowing components (e.g., positioner, arm 206, electronics, cooling mechanism for the block, etc.) to be accommodated within a limited space. In some cases, spacing the blocks 200 away from each other also facilitates cooling of the blocks via radiation convection.

Figure 3B:
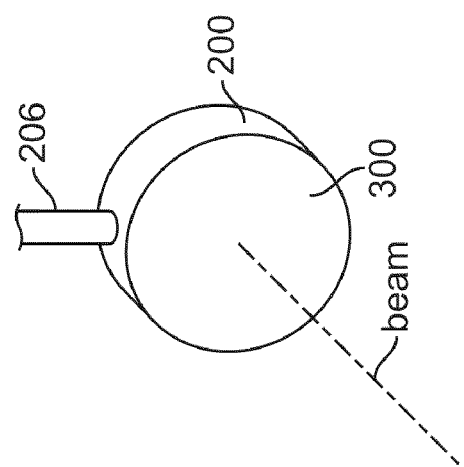
FIG. 3B illustrates a block of the energy modulator of FIG. 2 in accordance with other embodiments.
Figure 3A:
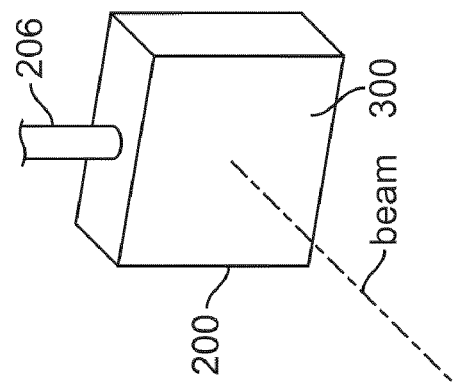
FIG. 3A illustrates a block of the energy modulator of FIG. 2 in accordance with some embodiments.

FIG. 3A illustrates a perspective view of one of the blocks 200 in accordance with some embodiments. As shown in the figure, the block 200 is a rectangular block with a rectangular cross section in the direction of the beam. The block 200 has a surface 300 that is substantially perpendicular (e.g., 90°±5°) to the beam. The surface 300 is substantially parallel to an opposite surface. Such configuration is beneficial in that it allows the beam to be filtered through the block 200 without steering effect (which may result if a wedge-like block is used). In other embodiments, the block 200 can have other shapes. For example, in other embodiments, the block 200 may have a circular cross section in the direction of the beam (FIG. 3B). In this embodiment, the block 200 also has a surface 300 that is substantially perpendicular to the beam.

Figure 4:
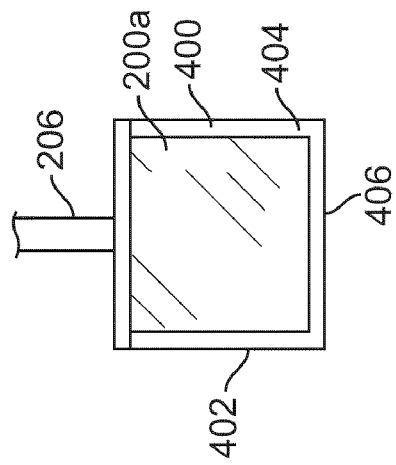
FIG. 4 illustrates a frame for providing structural integrity for a block of an energy modulator.

It should be noted that any of the blocks 200 needs not have a block-like configuration, and that it may have a non-block-like configuration, such as a structure with a thin profile. Thus, the term "block" should not be limited to structures having a block-like configuration, and may include structures having a thin or low profile such that a dimension on one side of the structure is substantially less than the dimension on another side. For example, block 200a in FIG. 2 may have a low profile because its thickness 202a is very small. In some cases, the energy modulator 14 may further include a frame 400 to which the block 200a (or another block with a thin profile) may be mounted (FIG. 4). The frame 400 provides structural integrity for the block 200a so that the block 200a does not bend or deform during use. The frame 400 includes a firs side 402, a second side 404, and a bottom side 406. In some embodiments, the frame 400 may not include the bottom side 406.

Returning to FIG. 2, the energy modulator 14 further includes a cooling system 220 for cooling some or all of the blocks 200. The cooling system 220 includes a fluid source 222 for delivering cooling fluid to channel(s) 224 within each of the blocks 200 via pipe(s) 226. In some embodiments, two or more blocks 200 may share the fluid source 222. In other embodiments, any one of the blocks 200 may have its own fluid source 222. For blocks 200 that may be too thin to incorporate cooling channel(s), the cooling system 220 may include a fan system 240 for delivering cooling air to cool the blocks 220 using convection. In other embodiments, the cooling of the entire set of blocks 200 may be performed using convection, in which case, the cooling system 220 does not include the fluid source 222 and the pipes 226, and includes only the fan system 240. In further embodiments, the cooling of any of the blocks 200 may be performed using radiation convection.

A method of using the system 10 that includes the energy modulator 14 will now be described. First information regarding a desired energy level for a proton beam is obtained. In some embodiments, such information may be a value of the desired energy level that is inputted into the processor 54 as a part of a treatment plan. In other embodiments, actual beam energy may be measured near the nozzle (e.g., via a chamber that measures monitor units), and the measured energy is compared with a desired level of energy to obtain a difference. In such case, the information regarding the desired energy level for a proton beam may be the difference value.

Next, if a proton beam has not been generated, the proton generator 12 generates protons and delivers a proton beam 280 towards the energy modulator 14. Based on the information regarding the desired energy level (which is associated with a level of energy for the beam that is desired to be provided downstream from the energy modulator 14), the processor 54 transmits signal(s) to the energy modulator 14 to cause one or more blocks 200 to be moved (via the positioning system 206) into, or away from, the path of the beam 280. In some embodiments, the energy modulator 14 may employ a lookup table for determining which block(s) 200 to use based on the amount of energy that is desired to be adjusted for the beam. In such cases, the lookup table has a first column containing values of different amount of energy that is adjustable by different combination of the block(s) 200. The lookup table also includes a second column containing identifier of block(s) 200 that correspond to each of the energy values in the first column. Examples of some of the entries for such lookup table are illustrated below:

| Index | Amount of energy desired to be adjusted (ΔE) | Block(s) to be positioned |
|---|---|---|
| 1 | 1.5 MeV | Block 2 |
| 2 | 14 MeV | Blocks 2, 5, 7 |
| 3 | 60 MeV | Blocks 4, 20 |

Thus, if the amount of energy ΔE desired to be adjusted is approximately 14 MeV, the processor 54 will determine from the lookup table that blocks with identifiers 2, 5, and 7 are to be positioned to provide such amount of energy modulation. The processor 54 then sends signal(s) to the positioner 206 to thereby position these blocks. In particular, the blocks will be removed from the path of the beam line if the amount of energy is to be incremented for the beam. Alternatively, the blocks will be placed into the beam path if the amount of energy is to be decreased for the beam. In other embodiments, instead of using a look-up table, the selection of the blocks may be determined using direction calculation technique.

In the example shown in the figure, block 200e and block 200g are moved down into the path of the beam 280 (see dashed lines of blocks 200e, 200g). Thus, the beam 280 is being modulated by the block 200e and block 200g in the example to achieve a desired level of energy. In some cases, the positioning system 206 is configured to position selected ones of the blocks 200 simultaneously, thereby allowing the energy of the beam to be adjusted efficiently. Alternatively, a subset of one or more of the blocks 200 may be positioned sequentially after another subset of block(s) 200 has been positioned. Such configuration allows energy of the beam at downstream to be measured after a first subset of block(s) 200 has been positioned. The measured energy may then be used as feedback, based upon which, the processor 54 may determine which block(s) in the second subset are to be positioned.

The above described method is performed when the nozzle 18 is at a certain position. If the nozzle 18 is mounted on a rotatable gantry, the above described method may be performed when the nozzle 18 is at a certain gantry angle, and may be repeated when the nozzle 18 is rotated to other gantry angles. In such cases, the operation of the energy modulator 14 is synchronized with the rotation of the nozzle 18. For example, when the nozzle 18 is at a certain gantry angle (at P1) at which the target region 23 is located deeper in the patient ($t_1$ at FIG. 9), the energy modulator 14 is operated to increase the energy of the beam such that the Bragg peak will be located deeper within the patient at the target region 23. On the other hand, when the nozzle 18 is at another gantry angle (at P2) at which the target region 23 is closer to the surface of the patient ($t_2$ at FIG. 9), the energy modulator 14 is accordingly operated to decrease the energy of the beam such that the Bragg peak will be located at the target region 23. In other embodiments, instead of rotating the nozzle 18 around the patient, the patient may be rotated relative to the nozzle 18 that is stationary.

During use of the energy modulator 14, the collimator 19 may be used to change the shape of the cross-section of the beam so that the beam conforms to the shape of the target region 23. In such cases, the nozzle 18 may further include a scatterer for spreading the proton beam before it reaches the collimator 19. The operation of the collimator 19 may be synchronized with the rotation of the gantry, thereby conforming the beam to the shape of the target region 23 from different gantry angles. In some embodiments, the operation of the collimator and the rotation of the nozzle 18 may be slaved to monitor units. In other embodiments, the system 10 may be configured to deliver pencil proton beam, in which case, the scatterer and the collimator may not be needed.

Figure 5:
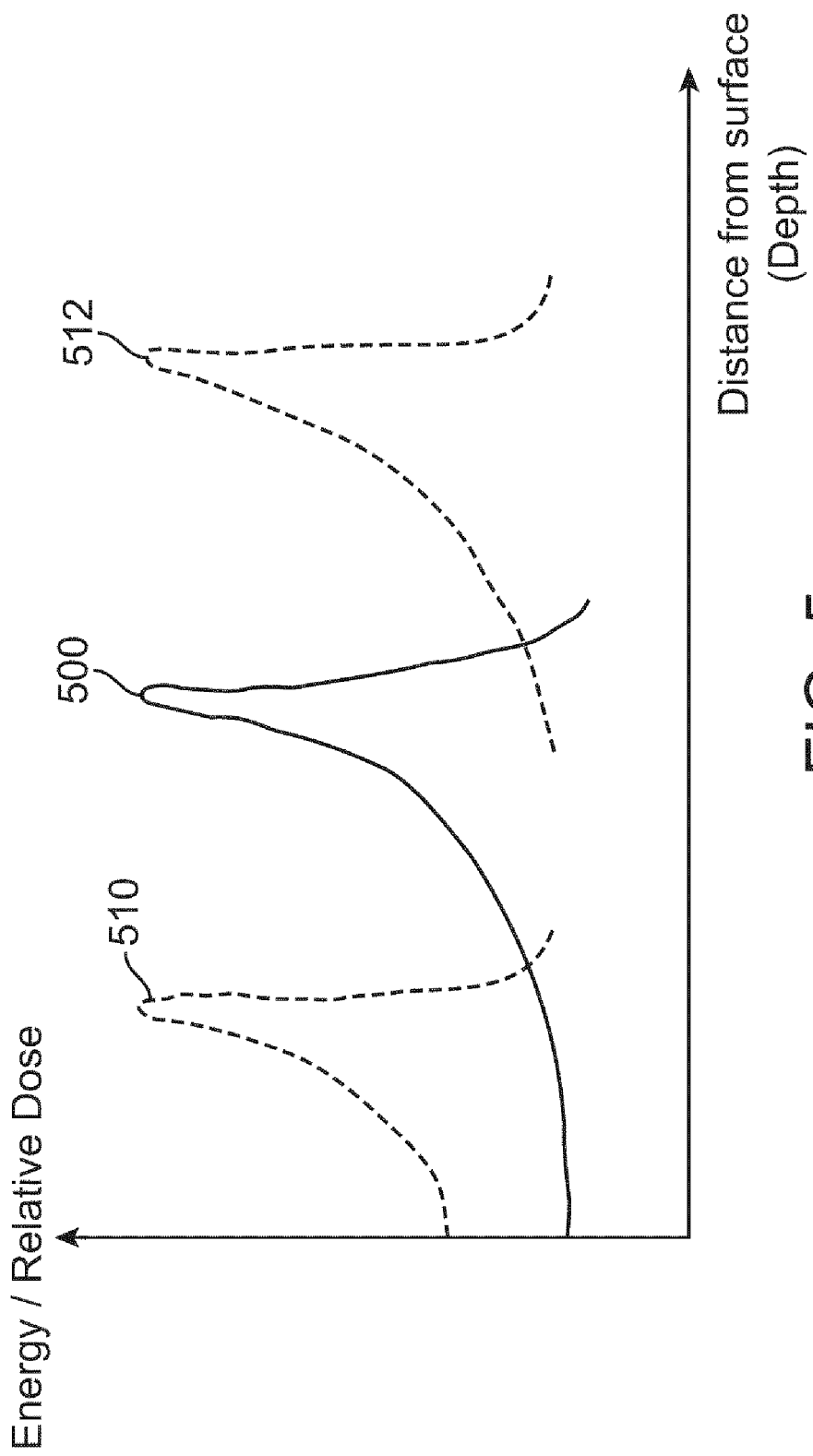
FIG. 5 illustrates an effect of using an energy modulator in accordance with embodiments described herein.

FIG. 5 illustrates an effect of using the block(s) 200 to modulate the beam energy. When a proton beam is delivered into matter, it results in a single Bragg peak curve 500. As illustrated by the Bragg peak curve 500, the energy is concentrated approximately at a location at which the beam ends. In accordance with embodiments described herein, when one or more of the blocks 200 are placed in the path of the beam, the block(s) 200 reduce the beam energy, thereby shifting the Bragg peak curve to a new position 510 (towards the left). On the other hand, when one or more of the blocks 200 are removed from the path of the beam, the beam energy increases, thereby allowing the beam to penetrate deeper, and shifting the Bragg peak curve to position 512 (towards the right).

During use of the energy modulator 14, the interaction between the beam 280 and the block(s) 200 may cause the block(s) 200 to heat up. The cooling system 220 is used to providing cooling for the block(s) 200—e.g., through the use of cooling fluid, and/or convection using the fan system 240.

In some cases, the interaction between the beam 280 and the block(s) 200 may create a scattering effect, thereby causing the beam exiting the block(s) 200 to diverge. In such cases, the energy modulator 14 may further include an emitance filter 282 having an opening 284. The emitance filter 282 is made from a material that blocks part of the diverged beam to thereby prevent the diverged beam from being transmitted downstream. The opening 284 at the emitance filter 282 allows part of the beam to be transmitted therethrough to the downstream direction.

As illustrated in the embodiments, the energy modulator 14 is advantageous because the logarithmic pattern of the blocks' thicknesses allows the energy of the beam to be modulated quickly. In particular, if an energy of the beam is desired to be adjusted (e.g., increased or decreased) by a relatively large increment, then blocks 200 with larger thicknesses may be used. On the other hand, if the amount of energy desired to be adjusted is small, then smaller blocks 200 may be used. Also, the energy modulator 14 allows the energy of the beam to be selectively and dynamically modulated during the treatment session. Further, the energy modulator 14 is advantageous because the blocks 200 do not need to be calibrated.

Figure 6:
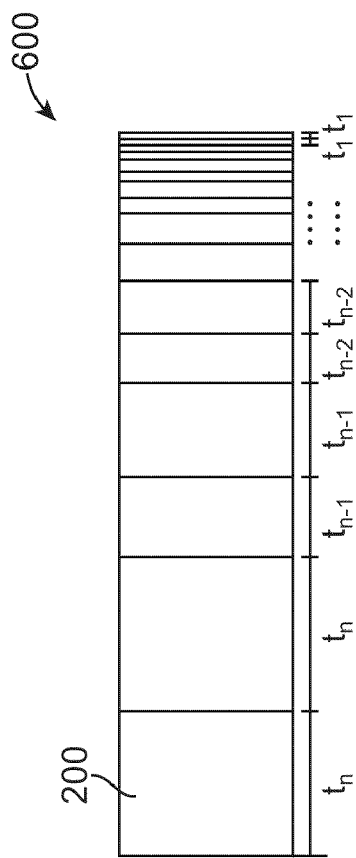
FIG. 6 illustrates an energy modulator in accordance with other embodiments.

FIG. 6 illustrates a set 600 of blocks 200 that may be used for the energy modulator 14 in accordance with other embodiments. The set 600 of blocks 200 is similar to that shown previously in that the blocks have thicknesses that form a logarithmic pattern. However, in the illustrated embodiments, the total number of blocks are twice as much as the embodiment of FIG. 2. In particular, there are two blocks 200 for each of the thicknesses. Such configuration is advantageous in that it provides more combination of the blocks 200, which in turn, more variations of the amount of energy modulation. In other embodiments, more than two blocks 200 may have the same thickness.

Figure 7:
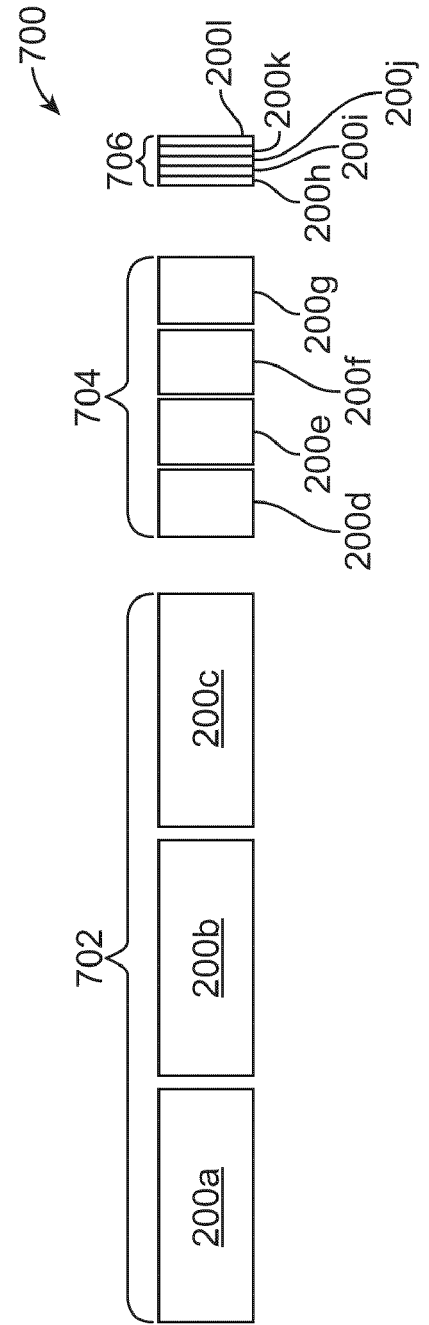
FIG. 7 illustrates an energy modulator in accordance with other embodiments.

In the above embodiments, the thicknesses of the blocks 200 measured in the direction of the beam form a logarithmic pattern in which at least some of the blocks 200 are two times in thickness of another block. However, in other embodiments, the thicknesses of the blocks 200 may have other patterns. FIG. 7 illustrates a set 700 of blocks 200 in accordance with other embodiments. The set 700 includes three subsets 702, 704, 706 of blocks 200. The first subset 702 includes three blocks 200a-200c, the second subset 704 includes four blocks 200d-200g, and the third subset 706 includes five blocks 200h-200l. In the illustrated embodiments, the blocks 200h-200l in the third subset 706 have the same thickness, and collectively have a combined thickness that is equal to the thickness of a block (e.g., block 200d) in the second subset 704. Also, the blocks 200d-200g in the second subset 704 have the same thickness, and collectively have a combined thickness that is equal to the thickness of a block (e.g., block 200a) in the first subset 702. Such configuration is advantageous in that it allows an energy of the beam to be modulated by a constant increment of energy within a range. The increment can be made more refined, e.g., by providing a group of blocks 200 having a smaller thickness in the direction of the beam. In other embodiments, the energy modulator 14 may have other number of subsets of blocks 200. Also, in other embodiments, each of the subsets 702, 704, 706 may have numbers of blocks that are different from the example shown. Also, in other embodiments, the blocks 200 in any of the subsets 702, 704, 706 may have different thicknesses within the subset. In further embodiments, the blocks 200 in each subset need not be arranged in a group, and may be commingled with blocks 200 in other subset(s). For example, the smaller blocks may be placed in between larger blocks, thereby allowing more room to accommodate the components (e.g., positioner, arm, etc.) associated with the smaller blocks.

Figure 8:
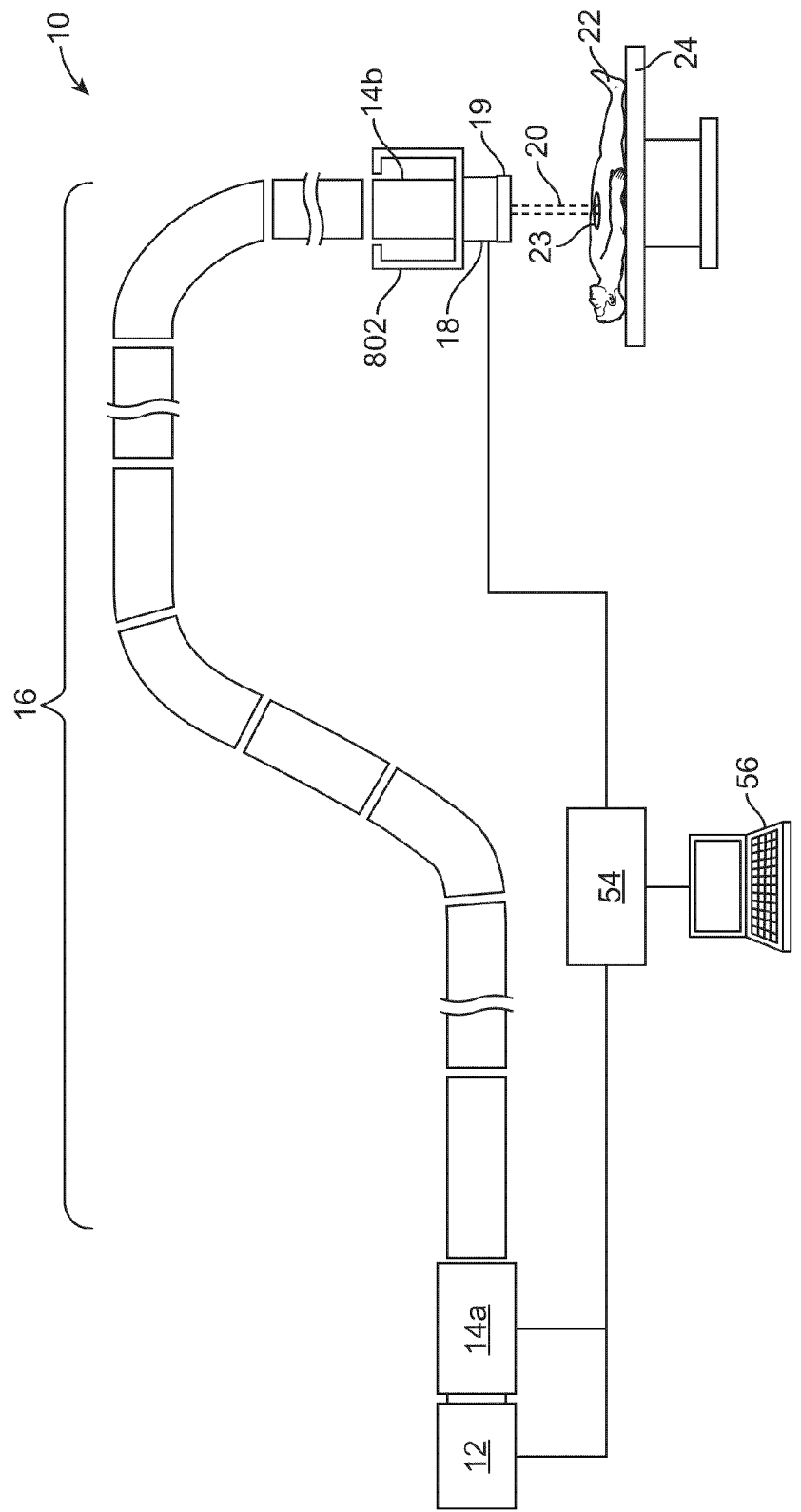
FIG. 8 is a block diagram of a proton system in accordance with other embodiments.

In the above embodiments, the proton system 10 has one energy modulator 14. However, in other embodiments, the proton system 10 may have a plurality of energy modulators 14. FIG. 8 illustrates a variation of the proton system 10 that includes two energy modulators 14a, 14b. As shown in the figure, the first energy modulator 14a is located at a position that is closer to the proton generator 12 than the nozzle 18, and the second energy modulator 14b is located at a position that is closer to the nozzle 18 than the proton generator 12. The proton system 10 may further include a shield 800 located near the nozzle 18. The shield 800 is for protecting the patient from neutrons that may be created as a result of the proton beam interacting with the blocks 200. Alternatively, the housing of the energy modulator 14b itself made be made from a material that functions as the shield. In other embodiments, the system 10 may include more than two energy modulators 14. For example, in other embodiments, the system 10 may include an energy modulator 14 anywhere along the beam transport system 16.

Figure 9:
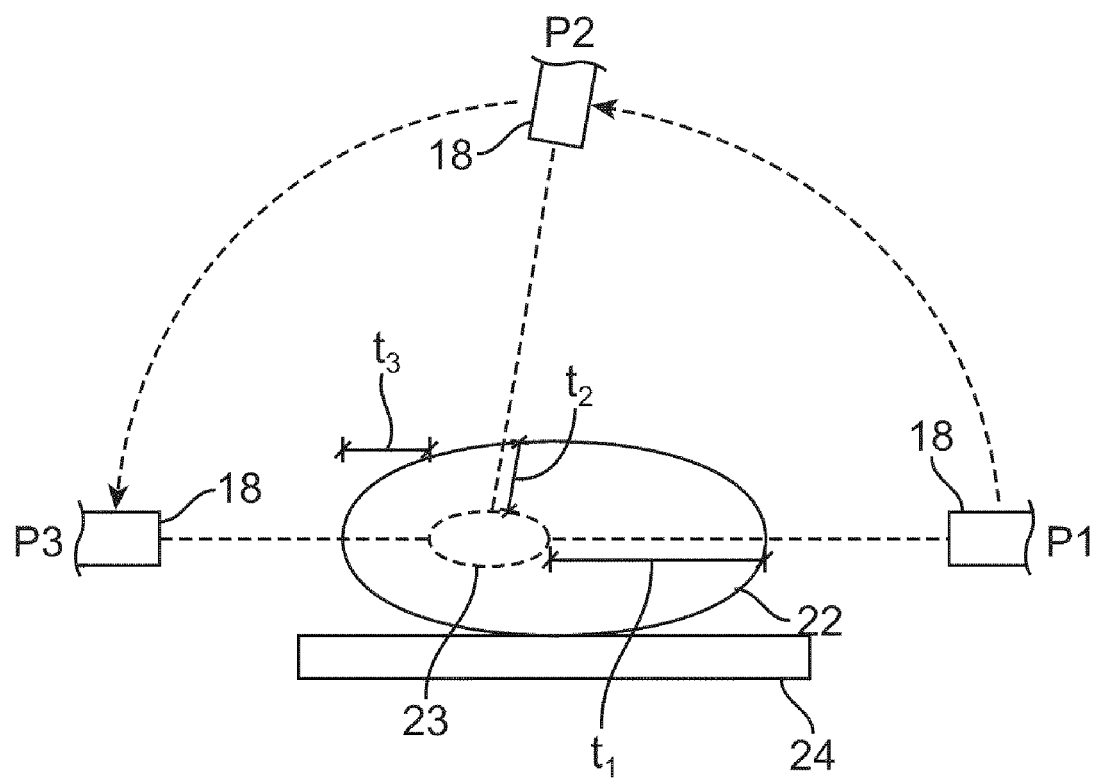
FIG. 9 illustrates a method of using the proton system of FIG. 8 in accordance with some embodiments.

During use of the system 10 of FIG. 8, the nozzle 18 is rotated about the patient 22 to deliver proton beam towards the target region 23 from a plurality of gantry angles (FIG. 9). Because the target region 23 is offset from the center of the patient 22, the proton beam at different gantry angles needs to penetrate different amount of tissue before reaching the target region 23. For example, the proton beam at one gantry angle (i.e., when the nozzle 18 is at position P1) needs to penetrate tissue of thickness=$t_1$, while at another gantry angle (i.e., when the nozzle 18 is at position P2), needs to penetrate tissue of thickness=$t_2$ which is thinner than $t_1$. In the illustrated embodiments, when the nozzle 12 is rotated from P1 to P2, the first energy modulator 14a may be used to decrease the energy of the beam by placing one or more blocks 200 in the first energy modulator 14a into the beam path. The operation of the first energy modulator 14a is similar to that described previously. When the nozzle 18 is rotated from P2 to P3, the amount of beam penetration needs to be increased to address the fact that there is an increasing amount of tissue that the beam needs to go through to reach the target region 23. In such cases, the second energy modulator 14b may be used to increase the energy of the beam by removing one or more blocks 200 in the second energy modulator 14b from the beam path. The operation of the second energy modulator 14b is also similar to that described previously. Sometimes, the magnetic components along the beam transport system 16, while allowing a beam with lower energy to be transported in a predictable manner, may not allow a beam with higher energy to be transported in a predictable manner. This is due to the hysteresis effect of the magnetic materials of the magnets that are in the beam transport system 16. As a result, without the second energy modulator 14b, in order to increase the beam transport to higher energy predictably, the energy acceptance of the magnet will need to be increased to a level that is higher than a desired level, and then the field must be adjusted downward to reach the magnetic field level for the desired beam energy. The use of the second energy modulator 14b obviates such need because the reduction of the beam energy is controlled by the second energy modulator 14b, which accounts for the hysteresis effect in the magnets of the beam transport system 16. Thus, the above technique is advantageous in that it allows an energy of the beam to be increased quickly and predictably. In other embodiments, instead of rotating the nozzle 18 around the patient, the patient may be rotated relative to the nozzle 18 that is stationary.

In other embodiments, instead of having two energy modulators 14a, 14b, the modulator 14a may be omitted- In such cases, the system 10 includes the modulator 14b at the distal end only.

In any of the embodiments described herein, the nozzle 18 may include additional components for altering the characteristic of the proton beam. For example, in some embodiments, the nozzle 18 may include a first scatterer for scattering the beam. Alternatively, instead of being part of the nozzle 18, the first scatterer may be upstream from the nozzle 18. In other embodiments, the nozzle 18 may include a second scatterer for further scattering the beam.

Figure 10:
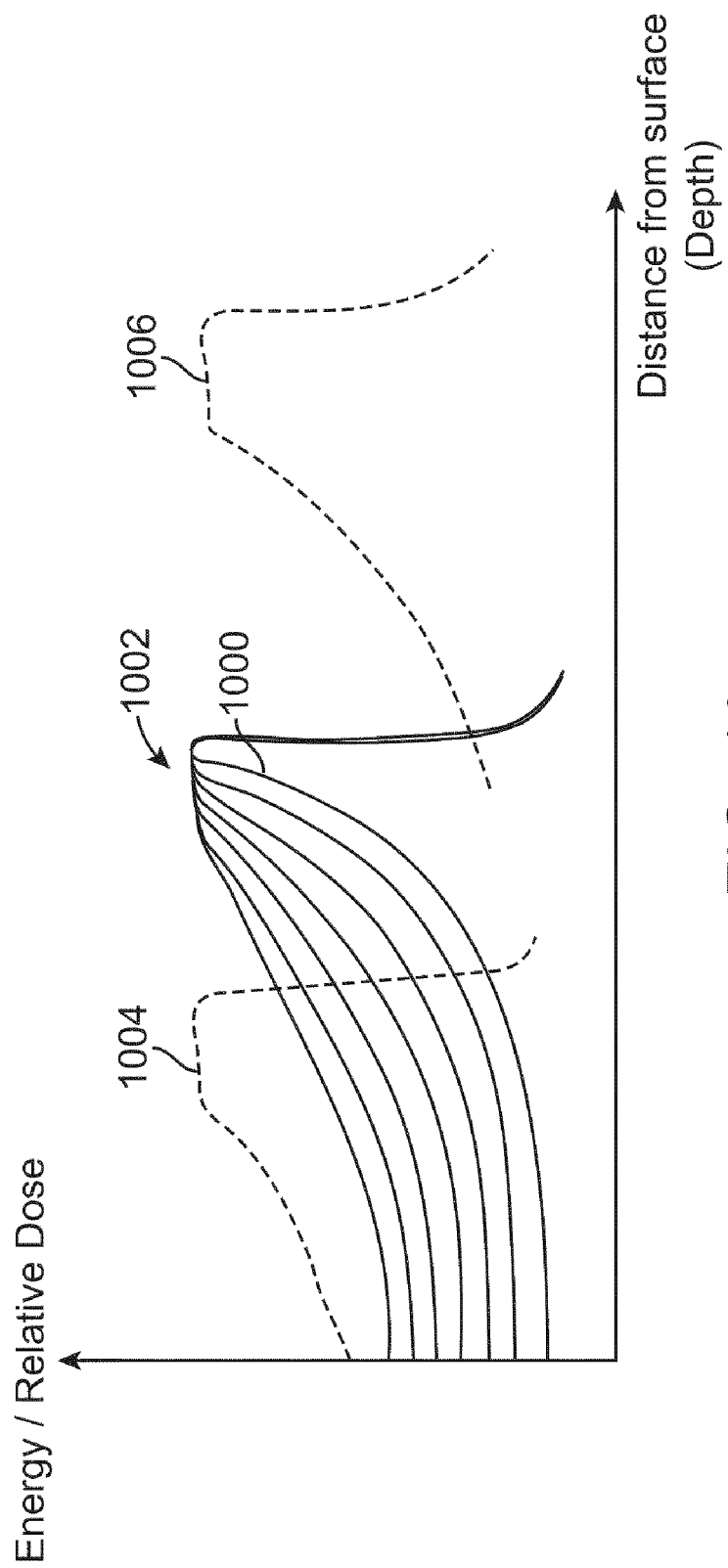
FIG. 10 illustrates an effect of using an energy modulator in accordance with embodiments described herein.

In some cases, the nozzle 18 may include a range modulator configured to spread the concentration of energy associated with the Bragg peak. For example, the range modulator may include a disk and a positioner for rotating the disk, wherein the disk has a step configuration such that different portions of the disk have different respective thicknesses. Alternatively, the range modulator may be a ridge filter. During use, the positioner places different portions of the disk (e.g., by rotating the disk) in front of the beam such that the beam is filtered by different portions of the disk that have different thicknesses. The thicker portions reduce the energy of the proton beam more than the relatively thinner portions. FIG. 10 illustrates an effect of using the block(s) 200 to modulate beam energy in a system that includes a range modulator. When a proton beam is delivered into matter, it results in a single Bragg peak curve 1000. As illustrated by the Bragg peak curve 1000, the energy is concentrated approximately at a location at which the beam ends. As a result of using the range modulator (which is pre-configured for spreading concentration of energy using all portions of the rotating disk), the beam has a spread out Bragg peak (SOBP) 1002. In accordance with embodiments described herein, when one or more of the blocks 200 are placed in the path of the beam, the block(s) 200 reduce the beam energy, thereby shifting the SOBP 1002 to the new position 1004 (towards the left). On the other hand, when one or more of the blocks 200 are removed from the path of the beam, the beam energy is increased, thereby shifting the SOBP 1002 to position 1006 (towards the right).

Also, in some embodiments, the system 10 may include a plurality of magnets for moving the proton beam. For example, in some embodiments, the system 10 may include two sets of orthogonal magnets for moving the proton beam, to thereby provide a scanning feature. The scanning may be done continuously or in a step-and-shoot manner.

Computer System Architecture

Figure 11:
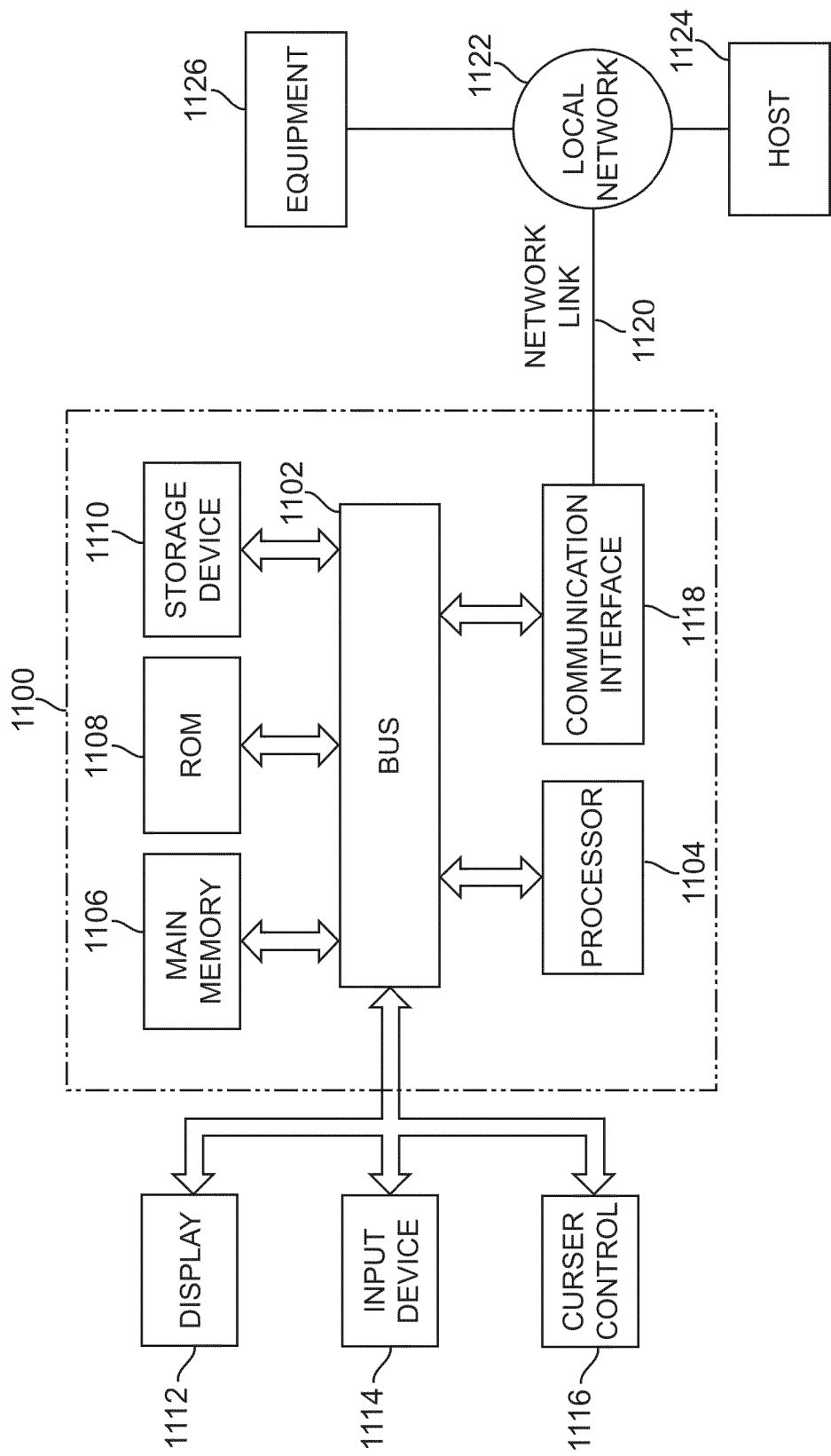
FIG. 11 is a block diagram of a computer system architecture, with which embodiments described herein may be implemented.

FIG. 11 is a block diagram that illustrates an embodiment of a computer system 1100 upon which an embodiment of the invention may be implemented. Computer system 1100 includes a bus 1102 or other communication mechanism for communicating information, and a processor 1104 coupled with the bus 1102 for processing information. The processor 1104 may be an example of the processor 54 of FIG. 1, or another processor that is used to perform various functions described herein. In some cases, the computer system 1100 may be used to implement the processor 54. The computer system 1100 also includes a main memory 1106, such as a random access memory (RAM) or other dynamic storage device, coupled to the bus 1102 for storing information and instructions to be executed by the processor 1104. The main memory 1106 also may be used for storing temporary variables or other intermediate information during execution of instructions to be executed by the processor 1104. The computer system 1100 further includes a read only memory (ROM) 1108 or other static storage device coupled to the bus 1102 for storing static information and instructions for the processor 1104. A data storage device 1110, such as a magnetic disk or optical disk, is provided and coupled to the bus 1102 for storing information and instructions.

The computer system 1100 may be coupled via the bus 1102 to a display 1112, such as a cathode ray tube (CRT) or a plat panel, for displaying information to a user. An input device 1114, including alphanumeric and other keys, is coupled to the bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

The computer system 1100 may be used for performing various functions (e.g., calculation) in accordance with the embodiments described herein. According to one embodiment, such use is provided by computer system 1100 in response to processor 1104 executing one or more sequences of one or more instructions contained in the main memory 1106. Such instructions may be read into the main memory 1106 from another computer-readable medium, such as storage device 1110. Execution of the sequences of instructions contained in the main memory 1106 causes the processor 1104 to perform the process steps described herein. One or more processors in a multi-processing arrangement may also be employed to execute the sequences of instructions contained in the main memory 1106. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1104 for execution. Such a medium may take many forms, including but not limited to, non-volatile media, volatile media, and transmission media. Non-volatile media includes, for example, optical or magnetic disks, such as the storage device 1110. Volatile media includes dynamic memory, such as the main memory 1106. Transmission media includes coaxial cables, copper wire and fiber optics, including the wires that comprise the bus 1102. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1104 for execution. For example, the instructions may initially be carried on a magnetic disk of a remote computer. The remote computer can load the instructions into its dynamic memory and send the instructions over a telephone line using a modem. A modem local to the computer system 1100 can receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1106, from which the processor 1104 retrieves and executes the instructions. The instructions received by the main memory 1106 may optionally be stored on the storage device 1110 either before or after execution by the processor 1104.

The computer system 1100 also includes a communication interface 1118 coupled to the bus 1102. The communication interface 1118 provides a two-way data communication coupling to a network link 1120 that is connected to a local network 1122. For example, the communication interface 1118 may be an integrated services digital network (ISDN) card or a modem to provide a data communication connection to a corresponding type of telephone line. As another example, the communication interface 1118 may be a local area network (LAN) card to provide a data communication connection to a compatible LAN. Wireless links may also be implemented. In any such implementation, the communication interface 1118 sends and receives electrical, electromagnetic or optical signals that carry data streams representing various types of information.

The network link 1120 typically provides data communication through one or more networks to other devices. For example, the network link 1120 may provide a connection through local network 1122 to a host computer 1124 or to equipment 1126 such as a radiation beam source or a switch operatively coupled to a radiation beam source. The data streams transported over the network link 1120 can comprise electrical, electromagnetic or optical signals. The signals through the various networks and the signals on the network link 1120 and through the communication interface 1118, which carry data to and from the computer system 1100, are exemplary forms of carrier waves transporting the information. The computer system 1100 can send messages and receive data, including program code, through the network (s), the network link 1120, and the communication interface 1118.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, in other embodiments, any of the embodiments of the energy modulator described herein may be used with a Linac. Also, in other embodiments, the system 10 needs not be a proton system, and may be other particle systems, e.g., systems that provide electron beams, neutron beams, or other particle beams. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for modulating an energy of a particle beam, comprising:
    providing a first modulator that is located closer to a particle source than a nozzle;
    providing a second modulator that is located closer to the nozzle than the particle source;
    operating the first modulator when an energy of the beam is desired to be decreased; and
    operating the second modulator when the energy of the beam is desired to be increased.

2. The method of claim 1, further comprising rotating the nozzle relative to a target region, wherein the operation of the first modulator is synchronized with the rotation of the nozzle.

3. The method of claim 2, wherein the operation of the second modulator is synchronized with the rotation of the nozzle.

4. The method of claim 1, wherein the act of operating the first modulator comprises inserting one or more blocks into a path of the particle beam.

5. The method of claim 4, further comprising:
    determining an amount of energy to be adjusted for the particle beam; and
    selecting the one or more blocks based on the determined amount of energy to be adjusted.

6. The method of claim 5, wherein the act of selecting the one or more blocks comprises performing a table lookup based on the determined amount of energy to be adjusted.

7. The method of claim 5, wherein the act of selecting the one or more blocks comprises performing a direction calculation.

8. The method of claim 1, wherein the act of operating the second modulator comprises removing one or more blocks from a path of the particle beam.

9. The method of claim 8, further comprising:
    determining an amount of energy to be adjusted for the particle beam; and
    selecting the one or more blocks based on the determined amount of energy to be adjusted.

10. The method of claim 9, wherein the act of selecting the one or more blocks comprises performing a table lookup based on the determined amount of energy to be adjusted.

11. The method of claim 1, further comprising providing a shield for protecting a patient from being irradiated by neutrons generated as a result of the operation of the second modulator.

12. The method of claim 1, further comprising cooling a component of the first modulator.

13. The method of claim 1, further comprising cooling a component of the second modulator.

14. The method of claim 1, wherein the first modulator comprises a plurality of blocks, the plurality of blocks having respective thicknesses that form a logarithmic pattern.

15. The method of claim 1, wherein the second modulator comprises a plurality of blocks, the plurality of blocks having respective thicknesses that form a logarithmic pattern.

16. The method of claim 1, wherein the first modulator comprises a first solid block, and the second modulator comprises a second solid block.

17. An energy modulator for use with a collimator and a particle source that provides a beam of particles, comprises:
    a first solid block moveable between a first position and a second position, wherein when the first solid block is at the first position, it is out of a path of the beam, and wherein when the first solid block is at the second position, it is in the path of the beam; and
    a second solid block moveable relative to the first block, wherein the second block and the first block are offset from each other in a direction of the beam;
    wherein the first block has a first energy absorption characteristic, and the second block has a second energy absorption characteristic that is different from the first energy absorption characteristic; and
    wherein the first solid block and the second solid block are located upstream from the collimator.

18. The energy modulator of claim 17, wherein the first solid block has a first thickness, and the second solid block has a second thickness that is different from the first thickness.

19. The energy modulator of claim 17, wherein the first solid block has a thickness, and the second solid block has a thickness that is two times the thickness of the first solid block.

20. The energy modulator of claim 17, wherein the first solid block is made from a first material, and the second block is made from a second material that is different from the first material.

21. The energy modulator of claim 17, wherein the first solid block is made from a first material and has a first thickness, and the second solid block is made from a second material and has a second thickness, the second material being different from the first material, and the second thickness being different from the first thickness.

22. The energy modulator of claim 17, wherein the first solid block is made from a material that is at least partially transparent to the beam.

23. The energy modulator of claim 17, further comprising a third solid block, wherein the first, second, and third solid blocks are offset relative to each other in a direction of the beam.

24. The energy modulator of claim 23, wherein the first solid block has a first thickness in a direction of the beam, the second solid block has a second thickness in the direction of the beam, and the third solid block has a third thickness in the direction of the beam; and
    wherein the first thickness, the second thickness, and the third thickness are different from each other.

25. The energy modulator of claim 24, wherein the third solid block has a thickness that is four times the thickness of the first solid block, and the second solid block has a thickness that is two times the thickness of the first solid block.

26. The energy modulator of claim 24, wherein the first thickness, the second thickness, and the third thickness form a non-linear pattern.

27. The energy modulator of claim 17, further comprising a positioner for moving the first solid block.

28. The energy modulator of claim 17, wherein a surface of the first solid block is perpendicular to the beam.

29. The energy modulator of claim 17, further comprising a mounting structure to which the first and the second solid block are slidably mounted.

30. The energy modulator of claim 29, wherein the mounting structure is mounted to a particle delivery system having the particle source, a particle transport system, and a nozzle.

31. The energy modulator of claim 30, wherein the mounting structure is mounted to the particle delivery system such that the mounting structure is closer to the particle source than the nozzle.

32. The energy modulator of claim 17, wherein the first solid block is made from a first material, the second solid block is made from a second material, and the second material has a Z value that is less then a Z value of the first material.

33. The energy modulator of claim 17, further comprising a cooling system coupled to the first solid block, the second solid block, or both.

34. The energy modulator of claim 17, further comprising an energy sensor, and a control coupled to the energy sensor, wherein the control is configured to adjust a position of the first solid block based on a feedback signal provided by the energy sensor.

35. The energy modulator of claim 17, wherein the particle source comprises a proton source.

36. The energy modulator of claim 17, wherein the first solid block and the second solid block are operable to attenuate the beam before the beam reaches the collimator.

37. The energy modulator of claim 17, further comprising a first end coupled to the particle source, and a second end coupled to a beam transport component.

38. The energy modulator of claim 37, wherein the first end is directly coupled to the particle source.

39. A method for modulating an energy of a particle beam, comprising:
    determining information regarding a desired particle beam energy;
    providing a set of at least three solid blocks, wherein the at least three solid blocks in the set are offset from each other in a direction of the beam, and are located upstream from a collimator;
    selecting one or more of the solid blocks from the set to be placed in a path of the beam based on the determined information; and
    placing the selected one or more of the solid blocks in the path of the beam.

40. The method of claim 39, wherein the particle beam comprises a proton beam.

41. The method of claim 39, wherein each of the at least three solid blocks in the set has a thickness that is different from the remaining solid blocks in the set.

42. The method of claim 41, wherein one of the solid blocks in the set has a thickness that is two times a thickness of another one of the solid blocks in the set.

43. The method of claim 39, wherein the solid blocks in the set are at least partially transparent to the beam.

44. The method of claim 39, wherein each of the solid blocks has two surfaces that are parallel to each other.

45. The method of claim 39, wherein one of the solid blocks has a Z value that is different from a Z value of another one of the solid blocks.

46. The method of claim 39, further comprising cooling the selected one or more of the solid blocks.

47. The method of claim 46, wherein one of the solid blocks is cooled using liquid, and another one of the solid blocks is cooled using convection.

48. The method of claim 39, wherein the act of determining the information regarding the desired particle beam energy comprises obtaining the information from a treatment plan.

49. The method of claim 39, wherein the act of determining the information regarding the desired particle beam energy comprises:
    measuring an energy of a delivered beam; and
    determining a difference between the measured energy and a desired energy, wherein the information comprises the determined difference.

50. The method of claim 39, further comprising using the selected one or more of the solid blocks to attenuate the beam before the beam reaches the collimator.

51. The method of claim 50, wherein the set of at least three solid blocks is a part of an energy modulator having a first end and a second end, the first end coupled to a particle source, the second end coupled to a beam transport component; and
    wherein the method further comprises passing the beam to the transport component after the selected one or more of the solid blocks has been used to attenuate the beam.

52. The method of claim 51, wherein the first end of the energy modulator is directly coupled to the particle source.

* * * * *

UNITED STATES PATENT AND TRADEMARK OFFICE
CERTIFICATE OF CORRECTION

| | | |
|---|---|---|
| PATENT NO. | : 8,330,132 B2 | Page 1 of 1 |
| APPLICATION NO. | : 12/199698 | |
| DATED | : December 11, 2012 | |
| INVENTOR(S) | : Guertin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 909 days.

Signed and Sealed this
Eighteenth Day of November, 2014

Michelle K. Lee
*Deputy Director of the United States Patent and Trademark Office*